(12) United States Patent
Strong et al.

(10) Patent No.: US 9,998,236 B2
(45) Date of Patent: Jun. 12, 2018

(54) SYSTEM FOR TRANSMITTING AND RECEIVING ELECTROMAGNETIC RADIATION

(71) Applicant: Picometrix, LLC, Ann Arbor, MI (US)

(72) Inventors: Timothy Strong, Trenton, MI (US); Gregory Stuk, Saline, MI (US); Steven Williamson, Ann Arbor, MI (US)

(73) Assignee: PICOMETRIX, LLC, Ann Arbor, MI (US)

( * ) Notice: Subject to any disclaimer, the term of this patent is extended or adjusted under 35 U.S.C. 154(b) by 0 days. days.

(21) Appl. No.: 15/103,605

(22) PCT Filed: Dec. 17, 2014

(86) PCT No.: PCT/US2014/070729
§ 371 (c)(1),
(2) Date: Jun. 10, 2016

(87) PCT Pub. No.: WO2015/112284
PCT Pub. Date: Jul. 30, 2015

(65) Prior Publication Data
US 2016/0315716 A1 Oct. 27, 2016

Related U.S. Application Data

(60) Provisional application No. 61/917,151, filed on Dec. 17, 2013.

(51) Int. Cl.
*H04B 10/00* (2013.01)
*G01J 5/02* (2006.01)
(Continued)

(52) U.S. Cl.
CPC ......... *H04B 10/90* (2013.01); *G01N 21/3586* (2013.01); *H04B 10/114* (2013.01); *H04B 10/25* (2013.01)

(58) Field of Classification Search
CPC .. G01N 21/3586; H04B 10/114; H04B 10/25; H04B 10/90
(Continued)

(56) References Cited

U.S. PATENT DOCUMENTS 4,303,802 A * 12/1981 Cumpston .............. H04M 11/04
340/526
5,323,260 A * 6/1994 Alfano .................. H01S 3/0057
359/241

(Continued)

FOREIGN PATENT DOCUMENTS

EP 2803960 A1 11/2014

OTHER PUBLICATIONS

Jordens et al, Fibre-coupled terahertz transceiver head; Dec. 2008, Electronics Letters.*

(Continued)

*Primary Examiner* — Amritbir Sandhu
(74) *Attorney, Agent, or Firm* — Brinks Gilson & Lione

(57) ABSTRACT

A system for transmitting and receiving electromagnetic radiation includes a beam splitter and a transceiver. The beam splitter is configured to separate an optical pulse into a pump pulse and a probe pulse. The transceiver may include a transmitter switch and a receiver switch. The pump pulse is directed toward the transmitter switch and the probe pulse is directed towards the receiver switch. Electromagnetic radiation is emitted from the transceiver when the pump pulse strikes the transmitter switch. The electromagnetic radiation may be terahertz radiation in either a pulsed or continuous wave form.

20 Claims, 8 Drawing Sheets

(51) Int. Cl.
*H04B 10/90* (2013.01)
*G01N 21/3586* (2014.01)
*H04B 10/114* (2013.01)
*H04B 10/25* (2013.01)

(58) Field of Classification Search
USPC ........... 398/118, 128–131; 250/341.1, 338.1, 250/350, 351
See application file for complete search history.

(56) References Cited

U.S. PATENT DOCUMENTS

| | | | | |
|---|---|---|---|---|
| 5,347,601 A * | 9/1994 | Ade | ................... | G02B 6/12004 385/14 |
| 6,344,829 B1 * | 2/2002 | Lee | ................... | H01Q 1/525 343/753 |
| 6,816,647 B1 * | 11/2004 | Rudd | ................... | G01N 21/3581 250/208.4 |
| 7,291,839 B1 * | 11/2007 | Demers | ................... | G01J 3/42 250/338.1 |
| 7,345,279 B2 * | 3/2008 | Mueller | ................... | G01J 9/04 250/341.1 |
| 7,531,803 B2 * | 5/2009 | Mittleman | ................... | G01J 3/42 250/341.1 |
| 7,535,005 B2 * | 5/2009 | Demers | ................... | G01J 3/42 250/341.1 |
| 7,808,636 B2 * | 10/2010 | Schulkin | ................... | G01J 4/00 356/364 |
| 7,831,210 B1 * | 11/2010 | Freeman | ................... | H04B 1/0057 333/133 |
| 8,207,501 B2 * | 6/2012 | Katagiri | ................... | G01J 3/42 250/341.1 |
| 8,759,778 B2 * | 6/2014 | Rahman | ................... | G01J 3/02 250/341.1 |
| 9,029,775 B2 * | 5/2015 | Demers | ................... | G01J 3/10 250/339.07 |
| 9,178,282 B2 * | 11/2015 | Mittleman | ................... | G01N 21/3581 |
| 9,400,214 B1 * | 7/2016 | Demers | ................... | G01J 3/0256 |
| 2001/0038074 A1 * | 11/2001 | Zhang | ................... | G01J 11/00 250/341.8 |
| 2003/0138112 A1 * | 7/2003 | Doy | ................... | H03F 3/005 381/74 |
| 2003/0226969 A1 * | 12/2003 | Williamson | ................... | G01N 21/532 250/341.1 |
| 2005/0117502 A1 * | 6/2005 | Kanda | ................... | G11B 7/005 369/124.11 |
| 2005/0230625 A1 * | 10/2005 | Zhang | ................... | G01N 21/3581 250/341.1 |
| 2007/0146881 A1 * | 6/2007 | Tanaka | ................... | G02B 6/4246 359/485.06 |
| 2007/0159760 A1 * | 7/2007 | Clark | ................... | H02H 9/04 361/118 |
| 2007/0232241 A1 * | 10/2007 | Carley | ................... | H04B 1/44 455/83 |
| 2008/0179528 A1 * | 7/2008 | Demers | ................... | G01J 3/42 250/341.1 |
| 2009/0066948 A1 * | 3/2009 | Karpowicz | ................... | G01J 3/42 356/326 |
| 2009/0190933 A1 * | 7/2009 | Fichter | ................... | H04B 10/2513 398/159 |
| 2009/0200472 A1 * | 8/2009 | Gregory | ................... | G01J 3/10 250/339.07 |
| 2009/0206263 A1 * | 8/2009 | Rahman | ................... | G01J 3/02 250/341.1 |
| 2009/0309645 A1 * | 12/2009 | Isaacson | ................... | G06G 7/186 327/337 |
| 2010/0277726 A1 * | 11/2010 | Logan, Jr. | ................... | G01J 3/10 356/326 |
| 2010/0280779 A1 * | 11/2010 | White | ................... | G01C 3/08 702/79 |
| 2010/0314545 A1 * | 12/2010 | Logan, Jr. | ................... | G01J 3/10 250/339.07 |
| 2012/0032083 A1 * | 2/2012 | Itsuji | ................... | G01J 3/42 250/350 |
| 2013/0004132 A1 * | 1/2013 | Chiu | ................... | G02B 6/4246 385/93 |
| 2013/0271763 A1 * | 10/2013 | Li | ................... | G01N 21/8806 356/365 |
| 2013/0334421 A1 * | 12/2013 | Itsuji | ................... | G01J 5/0205 250/341.8 |
| 2014/0097815 A1 * | 4/2014 | Fujisaki | ................... | H02M 1/36 323/283 |
| 2017/0023469 A1 * | 1/2017 | Zimdars | ................... | G01N 21/3581 |

OTHER PUBLICATIONS

Nagel et al; Terahertz transceiver microprobe for chip-inspection applications using opto-electronic time-domain reflectometry; Sep. 2013; IEEE.*
Jordens et al; Fibre-coupled Terahertz transceiver head; Dec. 2008 vol. 44 No. 25; Electronics letter.*
Nagel et al; Terahertz transceiver microprobe for chip-inspection applications using optoelectronic time-domain reflectometry; 2013; IEEE.*
Search Report and Written Opinion dated Aug. 18, 2015.
European Search Report dated Jul. 7, 2017.
C. Jördens, et al., "Fibre-coupled terahertz transceiver head," Electronics Letters, Dec. 4, 2008, vol. 44, No. 25.
Thorsten Göbel, et al., "Fiber-coupled on-chip THz transceiver," IEEE, 2009.
M. Nagel, et al., "Terahertz transceiver microprobe for chip-inspection applications using optoelectronic time-domain reflectometry," IEEE, 2013.

* cited by examiner

SYSTEM FOR TRANSMITTING AND RECEIVING ELECTROMAGNETIC RADIATION

CROSS REFERENCE TO RELATED APPLICATIONS

This application is a nationalization of PCT Serial No. PCT/US2014/070729, filed Dec. 17, 2014 which claims benefit of U.S. Provisional Application Ser. No. 61/917,151, filed Dec. 17, 2013.

FEDERALLY SPONSORED RESEARCH OR DEVELOPMENT

This invention was made with United States Government support under contract NNX12CA81C awarded by National Aeronautics and Space Administration (NASA). The United States Government has certain rights in the invention.

BACKGROUND

1. Field of the Invention

This invention relates to transceivers for transmitting and receiving electromagnetic radiation, and more particularly to transceivers for transmitting and receiving terahertz radiation.

2. Description of Related Art

A terahertz pulse can be produced by a device when a high speed optical pulse strikes a photoconductive switch generating electron-hole pairs in the semiconductor that causes the resulting charge carriers to flow between the photoconductive portion of a radiating antenna. This in turn emits an electromagnetic pulse from the antenna. The charge carrier population is quickly extinguished when the optical pulse is removed because of the fast carrier trapping speed that results from deep level traps within the semiconductor. This causes the ultrafast terahertz electromagnetic response to occur. Typical semiconductors used include low temperature grown gallium arsenide, low temperature grown indium gallium arsenide, and other suitable materials with the properties described. The semiconductor materials are typically designed with a direct band gap of the energy appropriate to absorb the incoming optical pulse efficiently.

The receiving antennas that detect the emitted terahertz electromagnetic radiation are often similar in construction and dimension to the transmitting antennas. The primary difference between the receiving antenna and the transmitting antenna is that the receiving antenna receives the incoming electromagnetic radiation which forms a small, but measureable, electric field at the antenna's photoconductive gap or switch. The imposed voltage bias resulting from this electric field is read by closing the photoconductive switch in the receiving antenna and measuring the induced current.

These terahertz systems usually use a pump-probe method of operation. Essentially, two antennas are used. The transmitting antenna is "pumped" with an optical pulse and emits the terahertz radiation. The receiving antenna is "probed" by a second pulse precisely time delayed from the first pulse. This time delay is often variable allowing for the sampling of the terahertz wave after it has been modified by a target object at different delay times from the initiation of the terahertz wave. The entire resulting waveform can be reconstructed by scanning the time delay of the probe pulse relative to the pump pulse.

Referring to FIG. 1, a prior art system 10 is shown of a known pump probe system. As its primary components, this system 10 includes a transmitter 12 for transmitting terahertz radiation 14 and a receiver 16 for receiving a portion 18 of the terahertz radiation 14 emitted by the transmitter 12. Examples of modules for transmitting and receiving terahertz radiation are disclosed in U.S. Pat. No. 6,816,647, which is herein incorporated by reference in its entirety.

Optical pulses used to excite the transmitter 12 and the receiver 16 are provided by optical fibers 20 and 22 which may be single mode optical fibers. A lens 24 directs terahertz radiation 26 towards a plate or sample 28. The plate or sample 28 reflects terahertz radiation 30, to a pellicle 32, which in turn reflects the reflected radiation 30 towards the receiver 16. These modules are fiber pigtailed and deliver short ($10^{-14}$-$10^{-12}$ second) optical pulses to the high-speed photoconductive switches. In the case of the transmitter 12, the short optical pulse activates a switch to generate a pulse of terahertz ($10^{10}$-$10^{13}$ Hz) radiation 26. This system uses a partially-reflective beam splitter, such as the pellicle 32, to overlap the beam paths of the transmitted and received terahertz beams.

One problem with this configuration is that approximately 75% of the terahertz power is lost when transmitted and returning signals encounter the pellicle 32. The transmitted signal loses half of its signal when initially encountering the pellicle 32. Half passes through the pellicle 32 to the plate or sample 28 being probed, while the other half is reflected away and lost. The return signal 30 encounters the same loss, as half is reflected by the pellicle 32 to the receiver 16, while the other half passes through the pellicle 32 and hits the transmitter 12 and is lost. Further, the configuration of the system 10 is also bulky, expensive, and difficult to align. It also requires that the fibers 20 and 22 be matched in length to deliver pulses to the transmitter 12 and the receiver 16. These fibers 20 and 22 can be problematic in that timing fluctuations caused by temperature changes, vibration effects, or simply stress imposed by twisting or pulling is imparted on one fiber more than it is the other fiber.

SUMMARY

A system is described for transmitting and receiving electromagnetic radiation. This system includes a beam splitter and a transceiver. The beam splitter is configured to separate an optical pulse into a pump pulse and a probe pulse. The transceiver may include a transmitter switch and a receiver switch. The pump pulse is directed toward the transmitter switch and the probe pulse is directed towards the receiver switch. Electromagnetic radiation is emitted from the transceiver when the pump pulse strikes the transmitter switch. The electromagnetic radiation may be terahertz radiation in either a pulsed or continuous wave form.

The optical pulse may be provided to the beam splitter via a single optical fiber. The single optical fiber may be a polarization-maintaining fiber. The pump pulse and the probe pulse may be orthogonal and polarized when the optical pulse is in the polarization-maintaining fiber.

The transmitter switch and receiver switch may be generally separated from each other. The transmitter switch and receiver switch may each have a separate antenna or may share a single antenna. If a single antenna is utilized, the transmitter switch and receiver switch may be electrically isolated from each other by a high-pass capacitor.

The system may be used in a reflective type configuration wherein the transmitter receives at least a portion of the radiation that it transmitted and was reflected from a sample.

However, the system could also be used in a transmissive configuration, wherein two transceivers are used, each being located on opposite sides of a sample. A first transceiver would send electromagnetic radiation through the sample and to the second transceiver, while the second transceiver would send electromagnetic radiation through the sample and to the first transceiver.

Further objects, features and advantages of this invention will become readily apparent to persons skilled in the art after a review of the following description, with reference to the drawings and claims that are appended to and form a part of this specification.

DETAILED DESCRIPTION

Figure 1:
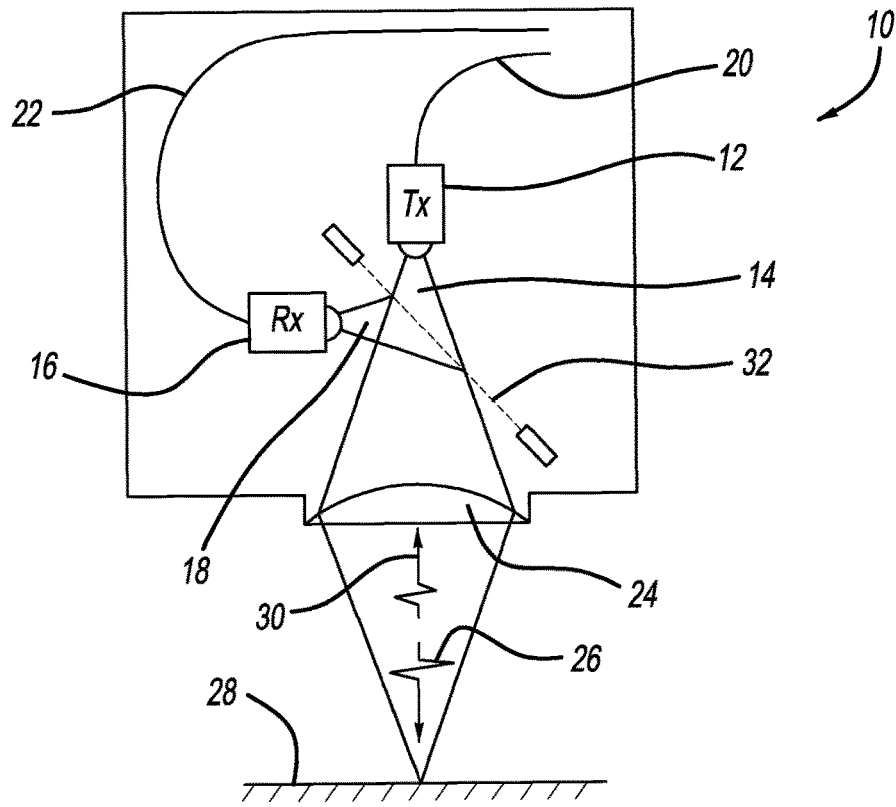
FIG. 1 illustrates a prior art system for transmitting and receiving terahertz radiation.
Figure 2:
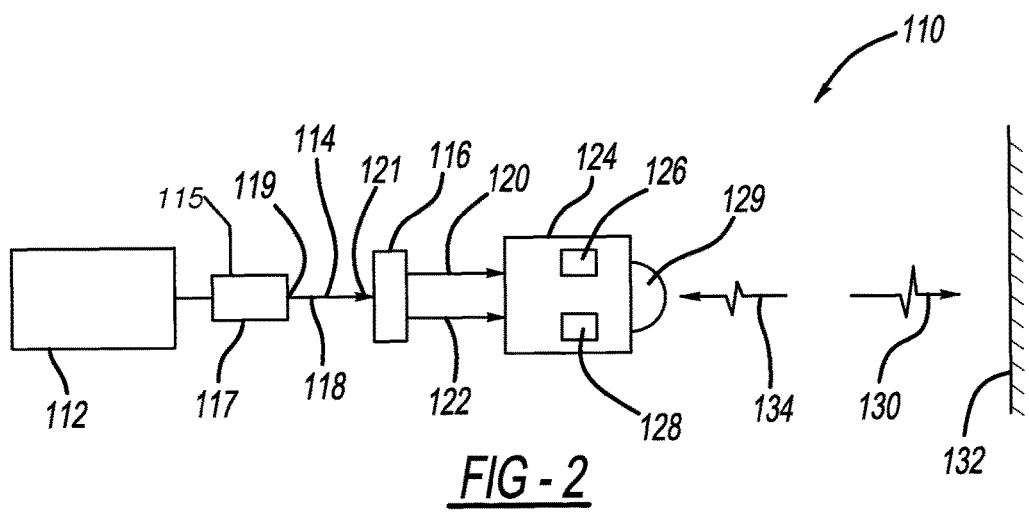
FIG. 2 illustrates a system for sending and receiving electromagnetic radiation.
Figure 3:
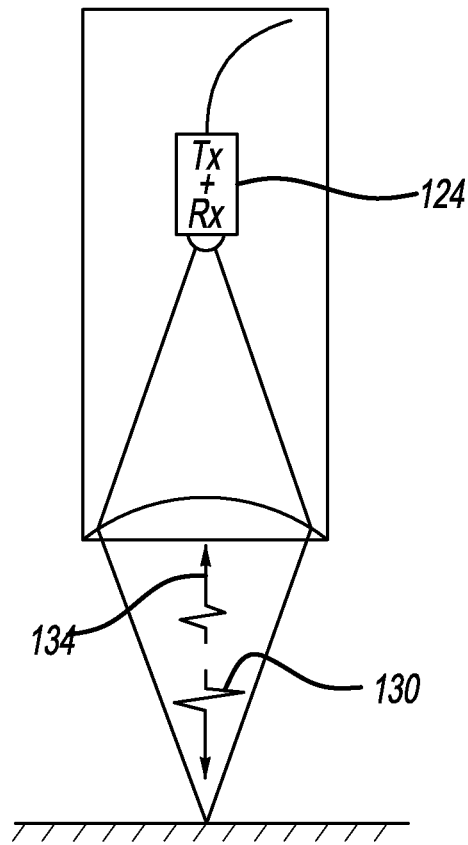
FIG. 3 illustrates a more detailed view of a transceiver for sending and receiving electromagnetic radiation.

Referring to FIGS. 2 and 3, a system 110 for sending and receiving electromagnetic radiation is shown. As its primary components, the system 110 includes a laser source 112 configured to output optical pulses 114. These optical pulses 114 may be provided to a pump and probe optical delay system and combined using a beam combiner, the output of which is provided to a beam splitter 116 that separates the pump and probe pulses. The optical pulses 114 may be provided to the beam splitter using an optical fiber 118. Generally, the optical fiber 118 may be polarization-maintaining optical fiber, but may also be single mode optical fiber. The optical pulses may include independent, orthogonally-polarized pump and probe laser pulses.

In the case that an optical fiber 118 is utilized, a dispersion precompensator 117 may be used to compensate for dispersion of the optical pulses 114 caused as the optical pulses 114 propagate through the optical fiber 118. An example of a dispersion precompensator is shown and described in U.S. Pat. No. 6,320,191, and is herein incorporated by reference in its entirety.

However, it should be understood that the optical pulses 114 may be provided to the beam splitter 116 through other means, not just those via an optical fiber 118. For example, the optical pulses 114 could be provided to the beam splitter 116 via free space or combination of free space and optical fibers. In the case a fiber 118 is utilized, the optical pulses 114 have two separate components, a pump pulse and a probe pulse that are arranged in an orthogonal manner. This allows two distinct optical pulses to be provided to the fiber 118.

The beam splitter 116 splits the optical pulses 114 into the pump pulse 120 and the probe pulse 122. A transceiver 124 receives the pump pulse 120 and a probe pulse 122. As will be described in more detail later, the transceiver 124 includes a transmitter switch 126 and a receiver switch 128. The transceiver 124 may be activated when an orthogonally-polarized pump pulse 120 and probe pulse 122 exit the fiber 118 and are demodulated, or spatially separated, by the beam splitter 116, which may be a birefringent window, causing the two pulses 120 and 122 to be directed to the transmitter switch 126 and the receiver switch 128, respectively.

The transceiver 124 may allow one or more fiber optical cables to enter and be mounted securely close to the antennas, with suitable lenses to concentrate the laser emissions onto the photo conductive switches or "gaps" of the antennas. Furthermore in this implementation electronics to amplify and perform signal processing are mounted inside the module.

The first laser pulse to exit the fiber 118, the pump pulse 120, is directed to the transmitter switch 126 which is integrated with a transceiver antenna system and emits a terahertz pulse 130 via a hyper hemispherical lens 129. The second pulse to exit the fiber, the probe pulse 122, is directed to the receiver switch 128 which is also integrated with the transceiver antenna system. A portion 134 of the transmitted terahertz signal 130 returning to the transceiver 124 via the hyper hemispherical lens 129 after reflection from a plate or sample 132 is received by the transceiver 124 and detected or sampled by the receiver switch 128 when excited with the probe pulse 122.

The transmitter and receiver switches 126 and 128 are integrated with the transceiver antenna system 124 and are spatially separated as well as electrically and optically isolated from each other. The preferred spacing between the switches 126 and 128 can range from as short as the wavelength of the laser (~1 um) to as long as the shortest measureable terahertz wavelength (~25 um on the substrate, assuming the refractive index of the substrate to be 3.5). This range in the spacing allows for good pump-probe separation to prevent cross talk while also allowing the transmitted 130 and received 134 terahertz signals to propagate distortion-free along essentially overlapping beam paths. The beam splitter 116 is fabricated to a thickness that separates the two focal spots by an amount equal to the spacing between the switches.

The orthogonally polarized pump and probe pulses 120 and 122 may have been previously combined at an input end 119 of the fiber 118 using a fiber optic polarizing beam combiner 115. After exiting from the output end 121 of the fiber 118, the pulses enter a beam splitter 116 which causes the orthogonally-polarized pulse trains to split into two parallel beams, the pump pulse 120 and the probe pulse 122. The pump pulse 120 and the probe pulse 122 form two spatially-separated spots when focused. The use of a single fiber 118 instead of two eliminates timing errors between the pump and probe pulses 120 and 122 that can occur from environmental factors, including fiber stress from stretching or twisting, vibration, temperature drift, etc. Though the optical pulses 120 and 122 could be spatially separated to activate the transducers, it is also possible to separate the beams using differing wavelengths or other, non-orthogonal polarization states.

The photoconductive gaps forming the switches 126 and 128 may be integrated at the midpoint of the antenna. The photoconductive switches 126 and 128 typically comprises a set of electrodes that form a gap on high-speed semiconductor material that is designed to have high resistivity when the switch is "open" or in the off-state and high conductivity when the switch is "closed" or in the on-state state, which occurs when activated by a laser pulse. The semiconductor material is characterized by its very short carrier lifetime that limits the duration of the switch's photo-initiated on state to a subpicosecond duration.

However, it should be understood that system 110 is applicable to photoconductive as well as electro-optic terahertz generation and sampling systems. For example, the system 110 could utilize an electro-optic terahertz generator with a photoconductive terahertz sampling gate or a photoconductive terahertz generator with an electro-optic sampling gate or have a photoconductive terahertz generator and sampling gate or have an electro-optic terahertz generator and sampling gate. It is not necessary for the transceiver 124 to comprise conventional antennas (i.e. dipole or spiral, etc.). It is possible, for example, for the transmitter to be based on the Cherenkov technique for generating a terahertz pulse within an electro-optic crystal and have the receiver use the same crystal to probe the terahertz signal by having the sampling optical pulse co-propagate with the incoming terahertz signal.

Further, use of an optical fiber 118 allows freedom of movement by providing a flexible umbilical of fiber optic 118 to guide the pulses 114 from the laser source 112 to the transceiver 124. Since the most commonly used source of the optical pulse trains is a fiber laser, it is possible to use such a laser as the laser source 112. The transceiver 124 may include amplification electronics as close to photoconducting antennas as possible to reduce noise, the umbilicals also typically have electrical conductors to provide power and conduct the resulting electrical signals to the rest of the system. The antenna assemblies also often contain various lens assemblies (typical silicon hyper hemispheres or polymer lenses). Precise timing of the pulses and control of the pulse length provides for higher resolution results. As such, frequently some form of dispersion compensation is required to account for dispersion in the two optical pulses as they travel along their orthogonally-polarized optical paths.

Figure 4:
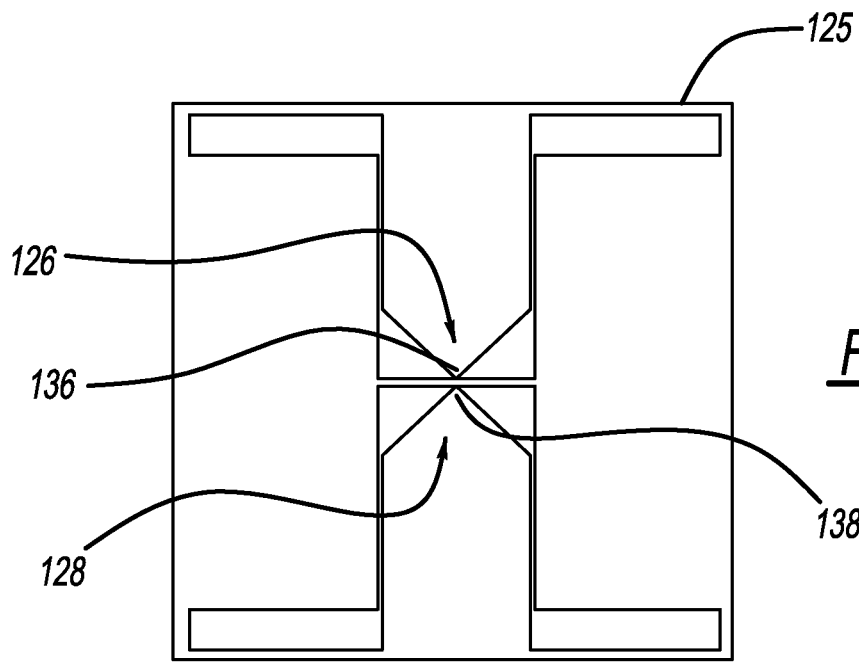
FIG. 4 illustrates a more detailed view of the transceiver having two antennas.
Figure 5:
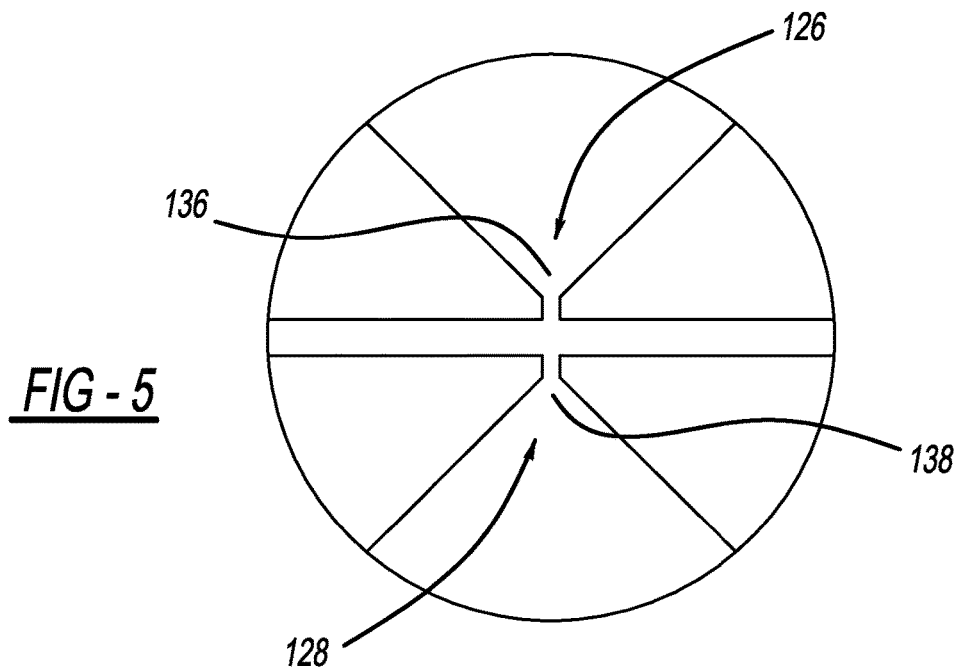
FIG. 5 illustrates a close-up view of the two antennas of the transceiver of FIG. 4.

Referring to FIGS. 4 and 5, FIG. 4 illustrates one example of a transceiver chip 125 which is part of the transceiver 124. Here, spatially-separated and electrically-isolated transmitter switch 126 and receiver switch 128 are shown at the midpoint of two bowtie antenna halves. As best shown in FIG. 5, the transmitter antenna 126 is the half-bowtie on the top while the receiver antenna 128 is the half-bowtie antenna on the bottom. As stated before, the pump pulse 120 and the probe pulse 122 are focused onto the transmitter switch 126 and receiver switch 128, respectively. The separation between the antennas 136 and 138, and thus the transmitter switch 126 and receiver switch 128, is on the order of 10 micrometers. Their photoconductive gaps are on the order of 1 micrometer.

Figure 6:
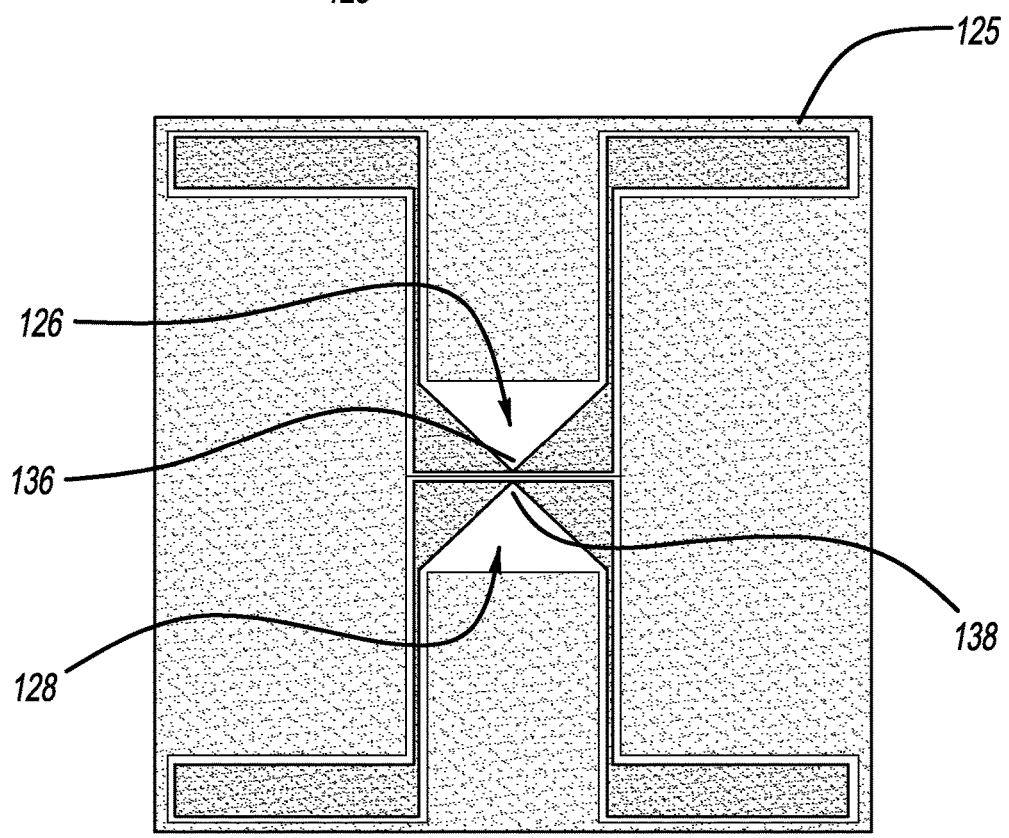
FIG. 6 illustrates a more detailed view of the transceiver having two antennas with variations in a guard band or shield positioned between transmitter and receiver antenna halves.

Given their close proximity, the two bowtie halves perform as a single antenna at terahertz frequencies. The 1000-fold difference between the optical and terahertz wavelengths enables thus the transmitter switch 126 and receiver switch 128 to be physically separated as well as electrically and optically isolated without significantly degrading terahertz performance. Referring to FIG. 6, additional isolation, shown in grey, may be provided by a guard band or shield positioned between the transmitter and receiver antenna halves. Variations in a guard band or shield positioned between the transmitter and receiver antenna halves are equally applicable to the other examples described in this description. This enables a high-gain amplifier to be incorporated in the receiver switch 128 without it being saturated by the transmitter switch 126. The transmitter switch 126 has a relatively large DC bias applied across its gap for generating the initial terahertz pulse. By isolating the transmitter switch 126 and receiver switch 128, no DC voltage is applied across the receiver switch 128, eliminating shot noise and laser fluctuation noise and yielding the highest possible signal-to-noise from the receiver switch 128. Note also that the two antennas 126 and 128 can be configured as dual transmitters or dual receivers or a combination of one transmitter and one receiver.

Figure 7:
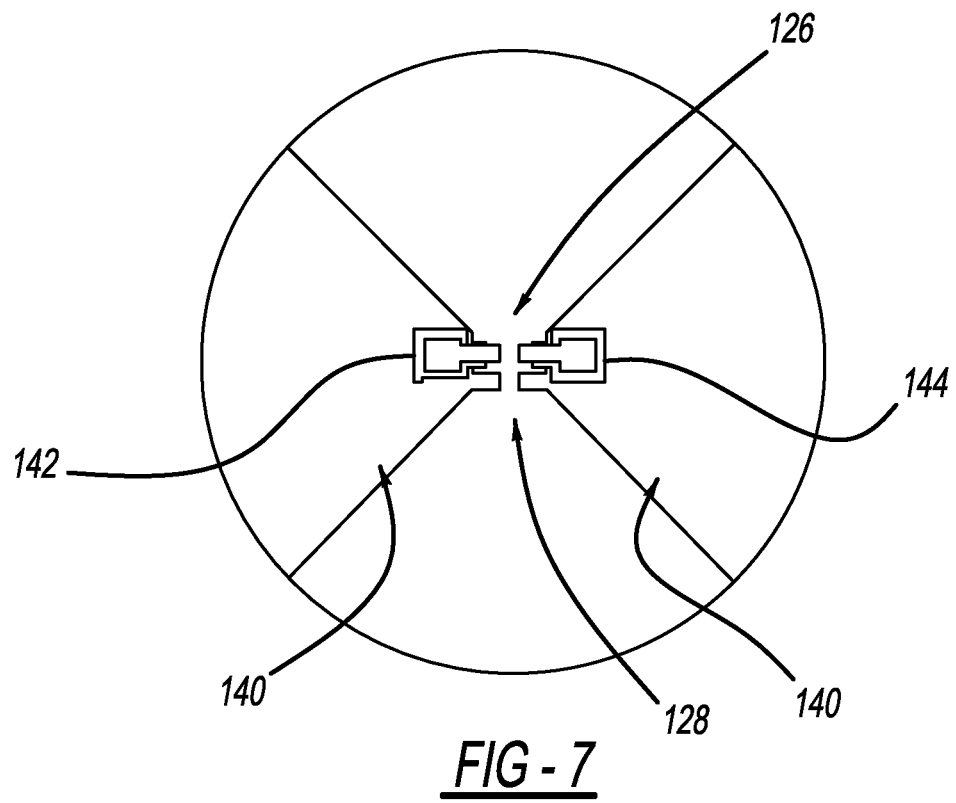
FIG. 7 illustrates a close-up view transceiver having a single antenna.

FIG. 7 shows another example of the transceiver chip 125. Depicted is a single, full-size, bow tie terahertz antenna 140 with the spatially-separated and electrically-isolated transmitter switch 126 and receiver switch 128 integrated into one antenna gap. The bias for the transmitter switch 126 is applied across the dielectric layers and between the photoconductive gap. Depending on the biasing arrangement, one or both sides of the switch can be isolated. Here, both sides are isolated FIG. 7. As in FIGS. 4 and 5, the separation between the two switches 126 and 128 is on the order of 10 micrometers while their photoconductive gaps are on the order of 1 micrometer.

The dimensions of the transmitter bias pads are kept small to reduce parasitic losses. With the bias applied and the pump pulse 120 striking the photoconductive gap, the gap's conductivity drops to tens of ohms and a subpicosecond electrical pulse couples through the insulating layers to the antenna 140. The antenna 140 then radiates as normal, transmitting a terahertz pulse. The receiver switch 128 performs similarly as described above. If the coupling capacitor integrated into the transmitter switch 126 is adequately small, the signal measured by the receiver switch will be virtually distortion free. The transmitter switch 126 and receiver switch 128 may be electrically isolated from each other by high-pass capacitors 142 and 144.

Figure 8:
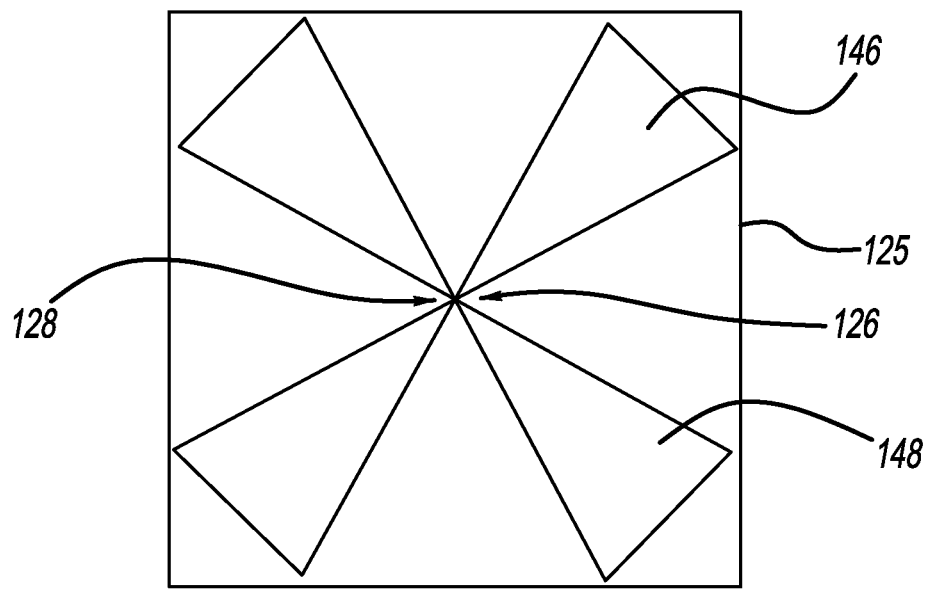
FIG. 8 illustrates a transceiver having orthogonally positioned antennas.
Figure 9:
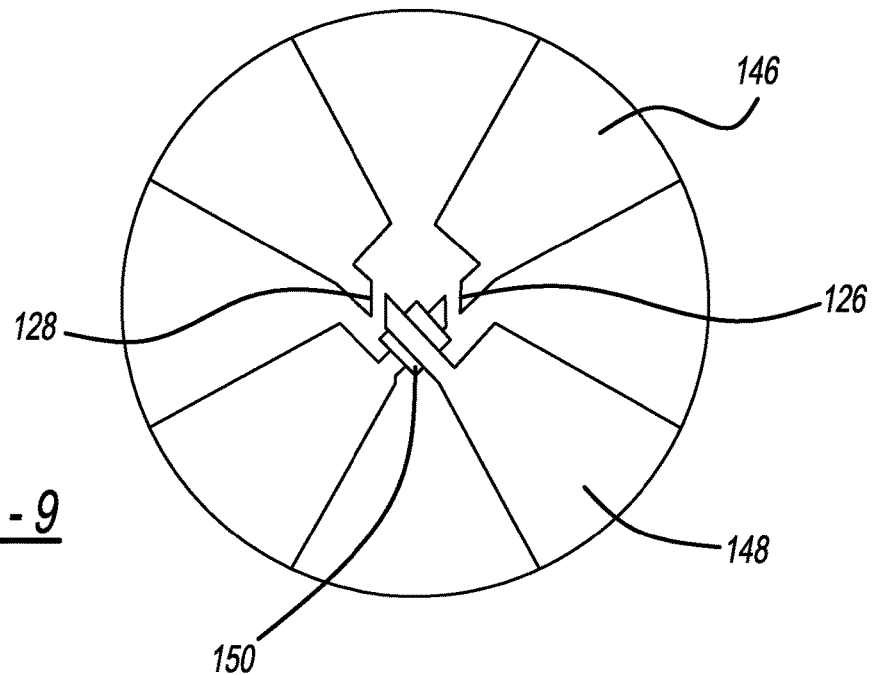
FIG. 9 is a close-view of the orthogonally positioned antennas of FIG. 8.

Referring to FIGS. 8 and 9, another example of the transceiver chip 125 is shown. Here, the antenna 146 for the transmitter switch 126 is orthogonal to the antenna 148 for the receiver switch 128. An insulating layer 150 is placed between the antennas 146 and 148. Essentially, the antennas 146 and 148 are 90 degrees to one another. That means the pump pulse 120 will produce polarized terahertz pulse that is orthogonal to the receiver antenna 148. Nothing may be received by the receiver antenna 148 unless the terahertz beam is altered from its orthogonally polarized state.

This is possible if the terahertz pulse propagates through birefringent media, such as would be caused by stress or fatigue in plastics, wood products or any other terahertz transparent media. Such an example would enable changes in birefringence to be detected and imaged to determine flaws in parts or materials. As long as the antennas 146 and 148 share a common center point and the switches 126 and 128 are adequately close in proximity and properly aligned to the pump and probe pulses 120 and 122, this orthogonal configuration can function distortion free. Furthermore, the angular (and thus polarization) relationship between the antennas 146 and 148 is not limited to aligned and orthogonal polarization states. Any angular relationship between the antennas 146 and 148 may be possible. Also, two antennas 146 and 148 can be configured as two transmitters or two receivers or a combination of one transmitter and one receiver.

Figure 10A:
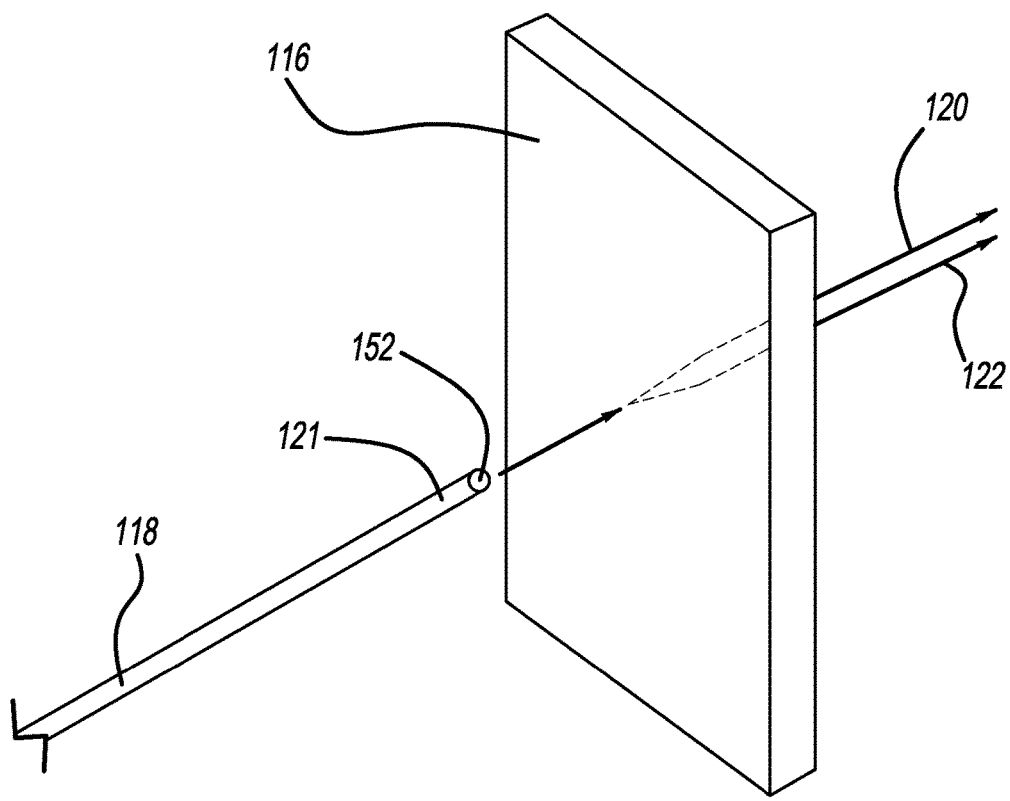
FIGS. 10A and 10B are illustrations of the beam splitter.
Figure 10B:
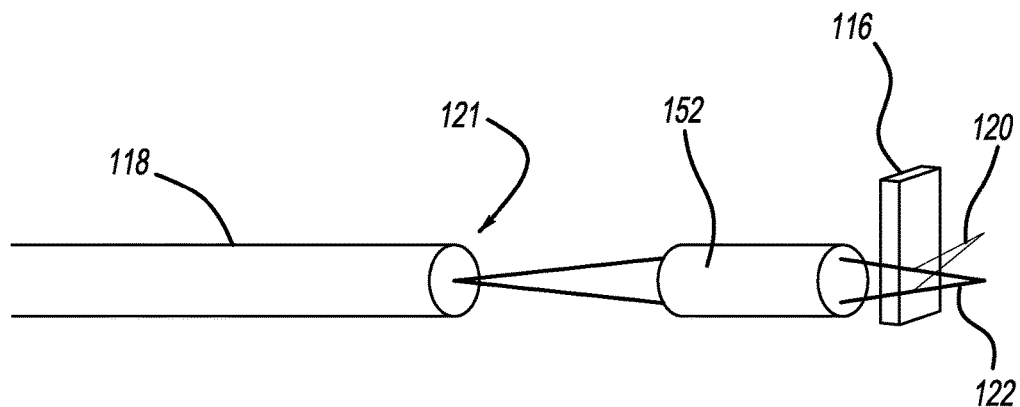

Referring to FIGS. 10A and 10B, more detailed views of the beam splitter 116 is provided. FIG. 10A is a conceptual drawing of the relationship between the polarized pump and probe pulses 120 and 122 and the beam splitter 116. The beam splitter 116 may be a birefringent crystal. The preferred crystal for the beam splitter 116 is yttrium orthovanadate ($YVO_4$), but other materials, such as calcite, may be used as well.

If the optical fiber 118 is a polarization-maintaining optical fiber, the optical fiber 118 allows linearly polarized optical pulses to propagate while maintaining their linear polarization state. Polarization-maintaining optical fiber has fast and slow axes orientated orthogonally to each other to support orthogonal polarization states. By using a polarization beam combiner on an input end of the fiber 118, it is possible to combine two separate polarization-maintaining fibers into a third polarization-maintaining fiber. Polarized pulses propagating in two separate fibers can then be combined into the single fiber 118 and propagate independently and orthogonally polarized to each other. This single fiber 118 can then support delivery of both the pump and probe pulses 120 and 122. In another embodiment, the pump pulse 120 and probe pulse 122 may not be orthogonal as long as the antennas 136 and 138 are tightly packed and could therefore be activated using two separate fibers or a single fiber having dual cores.

At the output end 121 of the fiber 118, the beam splitter 116 is used to separate the two polarization states corresponding to the pump and probe pulses 120 and 122. The beam splitter 116 separates the two orthogonally-polarized laser pulses 120 and 122 by laterally displacing the pulse polarized along the extraordinary axis of the beam splitter 116 from the pulse polarized along the ordinary axis. The thickness of the crystal used in the beam splitter 116 is one factor that determines the displacement of the focal points of the pump and probe pulses 120 and 122. The focal points of the pump and probe pulses 120 and 122 are set to match the spacing of the transmitter and receiver switches 126 and 128.

The beam splitter 116 is located between the output end 121 of the fiber 118 and the transmitter and receiver switches 126 and 128. Also included in this region is a focusing optic 152 that focuses the two beams down to spots sizes of the order of the gap dimension. Therefore, as the light exits the fiber 118 it is subjected to the focusing optic 152 and the beam splitter 116 that act together to focus and separate the two beams 120 and 122. The order of the focusing optic 152 and the beam splitter 116 is not critical. In one example, the beam splitter 116 is located between the focusing optic 152 and the transmitter and receiver switches 126 and 128. The focusing optic 152 may be a grin lens, as shown in FIG. 10B, or could be integrated with the optical fiber 118, as shown in FIG. 10A.

Alternate methods of separating the two pulses 120 and 122 are possible other than polarization, such as wavelength. Additionally, because the pump and probe pulses 120 and 122 are separated in time, one need not necessarily isolate the two pulses 120 and 122 physically as they are isolated temporally. If the pump pulse 120 is not physically separated from the probe pulse 122 at the antenna as described above, both pulse streams will impact on both antennas. While this means the receiver switch 128 is "active" when the terahertz pulse is launched from the transmitter switch 126, the travel time of the terahertz pulse from the separated antennas means that little terahertz energy will have arrived at the receiver switch 128 to be detected as noise. Simply stated, the separation of the two optical pulses 120 and 122 at the antenna describe one known implementation.

Figure 11:
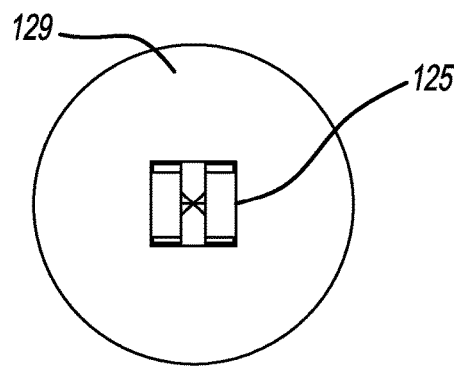
FIGS. 11-13 illustrate a detailed view of one embodiment of the transceiver installed on a system for sending and receiving radiation.
Figure 12:
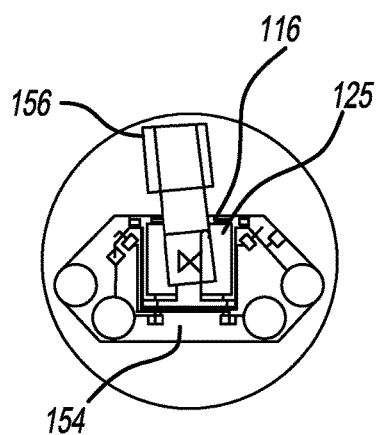

FIGS. 11-15 illustrate the transceiver 124. As best shown in FIG. 11, the transceiver chip 125 is shown mounted on the planar side of the silicon hyper hemispherical lens 129. FIG. 12 illustrates an alumina transition carrier 154 used to electrically connect the transceiver chip 125 to the transceiver circuit. Also shown is the beam splitter 116. The ability to rotate the beam splitter 116 enables precise alignment of the two laser spots of the pump and probe pulses 120 and 122 onto the transmitter and receiver switches 126 and 128. Alternatively, beam splitter 116 also need not be a separate component but could be integrated onto substrate of the transceiver chip 125.

Figure 13:
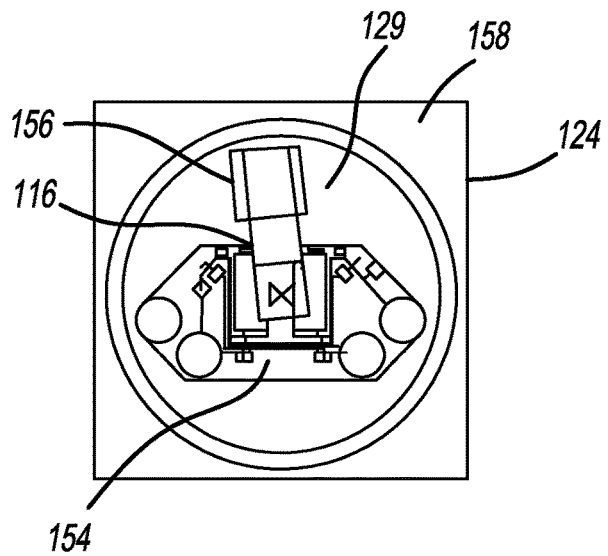
Figure 14:
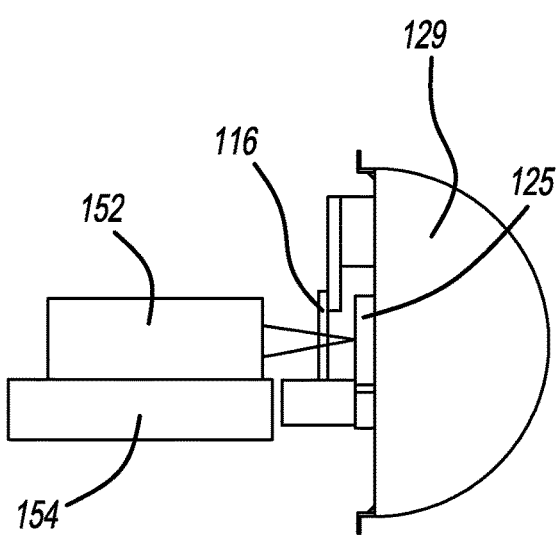
FIG. 14 is a side view of the system disclosed in FIG. 13.
Figure 15:
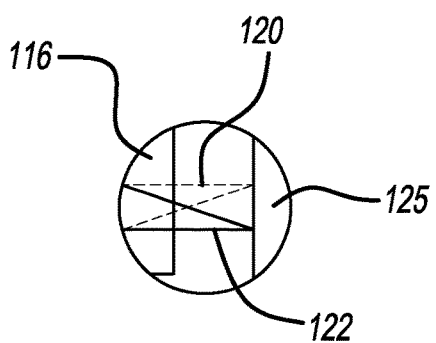
FIG. 15 is a more detailed view of the pump pulse and the probe pulse being provided to the transceiver.

FIG. 13 illustrates the transceiver assembly 124 on the hyper hemispherical lens 129 as it is mounted to a Kovar module front wall 158. FIG. 14, which is a side view of FIG. 13, shows the relationship between the focusing optic 152, preferably a grin lens, the beam splitter 116 and the transceiver chip 125. The expanded view, show in FIG. 15, shows how the two orthogonally polarized beams 120 and 122 are focused by the grin lens 152 and laterally separated by the beam splitter 116 as they arrive on the transceiver chip 125. The pump pulse 120 arrives first, hitting the transmitter switch 126, the probe pulse 122 arrives second hitting the receiver switch 128. The resulting assembly is mounted so that the switches 126 and 128 photoconductive transducers are placed as close to the focal point of the immersion hyper hemispherical silicon lens 129 as practical to collimate, or nearly collimate the emitted terahertz radiation and improve efficiency.

This is accomplished using optical radiation of a wavelength shorter that the terahertz wavelength. This allows the optical radiation to be spatially separated into a plurality of isolated beams 120 and 122 that then are used to generate and/or measure a plurality of terahertz signals, each having a wavelength or distribution of wavelengths that are substantially longer in dimension than the optical wavelengths (or wavelength) of the radiation that is activating the terahertz generating and receiving switches 126 and 128 thereby enabling all the plurality of terahertz signals to share a common beam path.

Figure 16:
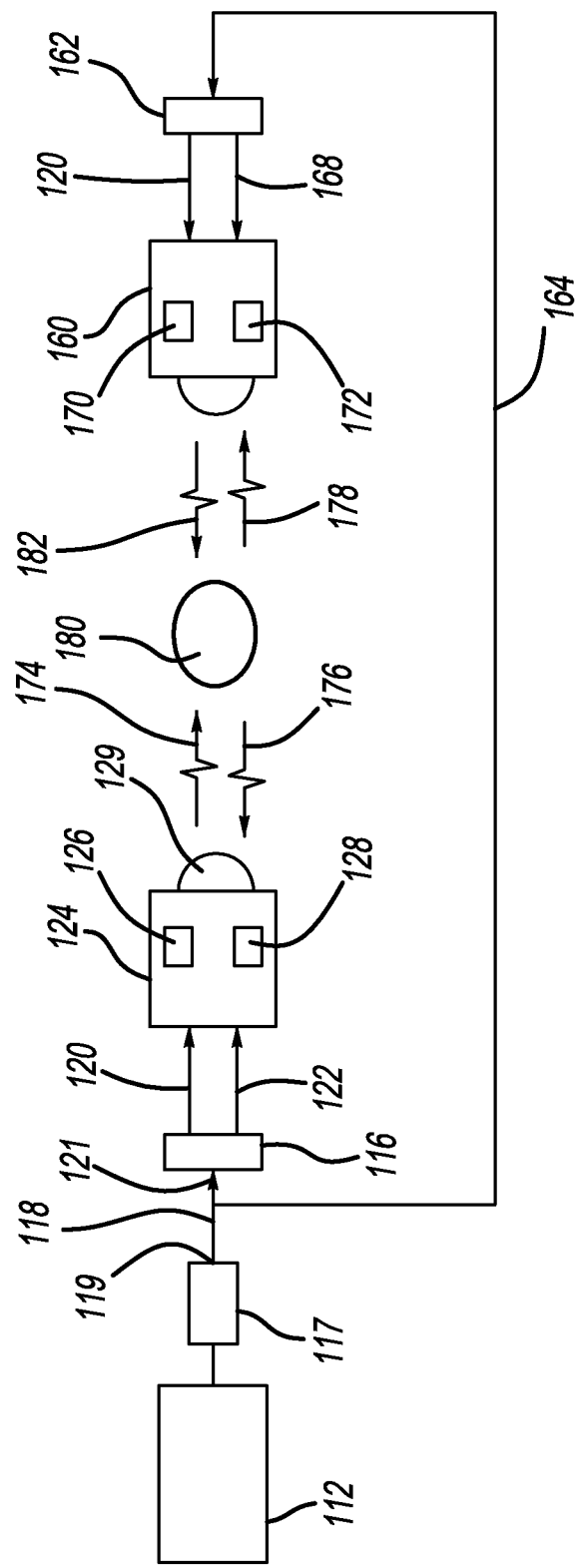
FIG. 16 illustrates a system for sending and receiving electromagnetic radiation, wherein this system is used in a transmissive type configuration.

Referring to FIG. 16, it is also possible to use two or more transceivers in one measurement configuration. The transceiver 160 is essentially a duplicate system of transceiver 124 and will not be described in detail as the description for the transceiver 124 is applicable. In this example, transceiver 160 receives shares the same laser source 112 as transceiver 124. A beam splitter 162, similar to beam splitter 116, receives the optical pulse 118 from a fiber 164 and separates the optical pulse into a pump pulse 166 and a probe pulse 168. Like with the transceiver 124, the pump pulse 166 is provided to a transmitter switch 170, while the probe pulse 168 is provided to receiver switch 172.

As an example, the transceiver 124 could radiate a terahertz pulse 174 with a portion 176 that is received by the receiver switch 128 and/or a portion 178 may be transmitted through a sample 180 to the receiver switch 172 located in the second transceiver 160 on the opposite side of the sample 180 under test. This second measurement is made in transmission mode. With this configuration, both reflection and transmission terahertz data can be obtained simultaneously from the sample 180. The reverse set of measurements is also possible and at the same time. That is, the second transceiver 160 in this configuration could also radiate a terahertz pulse 182. This pulse 182 could be measured in transmission mode by the first transceiver 124 as well as in reflection mode by the second transceiver 160. In total, four measurements, two in transmission and two in reflection could be made from the same point on the sample 166 and at the same time.

As such, any combination of generating and receiving terahertz signals from one system to another is possible, since all optical pulses used to activate the transmitter and receiver switches originate from the same laser source and are therefore exactly synchronized. It is also possible with this invention to use the pellicle configuration to have two transceivers mounted on either side of a sample. With this configuration, different terahertz polarizations could be used to measure a sample.

The resulting system confers several advantages over the typical system that uses two separate antenna systems. First, there are fewer materials required reducing cost and simplifying the implementation of a system. Only one module, hyper hemisphere, lens system, optical fiber, electronic umbilical etc. is required for the combination device. Another advantage is that if the system is used for reflective measurements, a system comprised of two separate antenna modules typically requires the use of a pellicle in the terahertz beam to overcome the fact that the transmitting antenna and receiving antenna cannot be in the same physical location.

The presence of the pellicle results in a loss of terahertz energy and adds complexity to the system. The two separate modules in such a system also require alignment to maximize the terahertz signal through the system. The system presented here eliminates the pellicle since the transmitter and receiver are in the same terahertz electromagnetic path, reducing losses and alignment requirements. The advantages of which are discussed in U.S. Pat. No. 8,436,310 incorporated herein by reference in its entirety.

As a person skilled in the art will readily appreciate, the above description is meant as an illustration of implementation of the principles this invention. This description is not intended to limit the scope or application of this invention in that the invention is susceptible to modification, variation and change, without departing from the spirit of this invention, as defined in the following claims.

The invention claimed is:

1. A system for transmitting and receiving electromagnetic radiation, the system comprising:
    a beam splitter configured to separate an optical pulse into a pump pulse and a probe pulse, wherein the pump pulse has a pump pulse focal spot and the probe pulse has a probe pulse focal spot;
    a transceiver having a transmitter switch and a receiver switch;
    wherein the pump pulse is directed towards to the transmitter switch and the probe pulse is directed towards the receiver switch;
    wherein the transceiver is configured to emit the electromagnetic radiation when the pump pulse strikes the transmitter switch and detect the electromagnetic radiation when the pump pulse strikes the receiver switch;
    a hemispherical lens, the hemispherical lens being configured to both direct the electromagnetic radiation emitted by the transceiver to a sample and direct the electromagnetic radiation from the sample to the transceiver; and
    wherein the beam splitter is configured to separate the pump pulse focal spot and the probe pulse focal spot by an amount equal to a spacing between the transmitter switch and the receiver switch.

2. The system of claim 1, further comprising a single optical fiber, wherein the optical pulse is provided to the beam splitter via the single optical fiber.

3. The system of claim 2, wherein the single optical fiber is polarization-maintaining fiber.

4. The system of claim 3, wherein the pump pulse and the probe pulse are orthogonally polarized when in the polarization-maintaining fiber.

5. The system of claim 2 further comprising a dispersion compensator in optical communication with the single optical fiber to compensate for a dispersion of the optical pulse caused as the optical pulse propagates through the single optical fiber.

6. The system of claim 1, wherein the electromagnetic radiation is terahertz radiation.

7. The system of claim 6, wherein the terahertz radiation is either continuous wave terahertz radiation or pulsed terahertz radiation.

8. The system of claim 1, wherein the transmitter switch and the receiver switch are separate from each other.

9. The system of claim 8, wherein the transmitter switch and the receiver switch are separated from each other by a distance of 1 micrometer to 1 millimeter.

10. The system of claim 1, wherein the transmitter switch and the receiver switch each have an antenna.

11. The system of claim 10, where the antenna for the transmitter switch is orthogonal to the antenna for the receiver switch.

12. The system of claim 1, wherein the transmitter switch and the receiver switch utilize a single antenna.

13. The system of claim 12, wherein the transmitter switch and the receiver switch are electrically isolated from each other by a high-pass capacitor.

14. The system of claim 1, wherein the beam splitter is a birefringent window.

15. The system of claim 14, wherein the birefringent window is made from either yttrium orthavanadate or calcite.

16. The system of claim 1, further comprising a focusing optic located between a single optical fiber and the beam splitter for focusing the optical pulse from the single optical fiber.

17. The system of claim 16, wherein the focusing optic is a grin lens.

18. The system of claim 1, wherein the transceiver is mounted on a planar side of the hemispherical lens.

19. The system of claim 1, wherein the receiver switch is configured to receive at least a portion of the electromagnetic radiation emitted by the transmitter switch and reflected from the sample.

20. The system of claim 1, further comprising a second transceiver, where the second transceiver is configured to receive at least a portion of the electromagnetic radiation emitted by the transmitter switch and through the sample.

* * * * *